United States Patent
Lavallee et al.

(10) Patent No.: US 12,171,509 B2
(45) Date of Patent: Dec. 24, 2024

(54) ROBOTIC SYSTEM FOR REMOVING BONY MATERIAL FROM AN ANATOMICAL STRUCTURE

(71) Applicant: DePuy Ireland Unlimited Company, Ringaskiddy (IE)

(72) Inventors: Stéphane Lavallee, Gieres (FR); Daniel Girardeau-Montaut, Gieres (FR); Francois Urvoy, Gieres (FR); Nicolas Demanget, Gieres (FR)

(73) Assignee: DePuy Ireland Unlimited Company, Ringaskiddy (IE)

( * ) Notice: Subject to any disclaimer, the term of this patent is extended or adjusted under 35 U.S.C. 154(b) by 945 days.

(21) Appl. No.: 17/056,330

(22) PCT Filed: May 28, 2019

(86) PCT No.: PCT/EP2019/063838
§ 371 (c)(1),
(2) Date: Nov. 17, 2020

(87) PCT Pub. No.: WO2019/229071
PCT Pub. Date: Dec. 5, 2019

(65) Prior Publication Data
US 2021/0205033 A1     Jul. 8, 2021

(30) Foreign Application Priority Data
May 28, 2018   (EP) .................................. 18305649

(51) Int. Cl.
*A61B 34/30*     (2016.01)
*A61B 17/16*     (2006.01)
(Continued)

(52) U.S. Cl.
CPC .......... *A61B 34/30* (2016.02); *A61B 17/1615* (2013.01); *A61B 17/1675* (2013.01);
(Continued)

(58) Field of Classification Search
CPC ......... A61B 34/30; A61B 34/25; A61B 90/06; A61B 17/1615; A61B 17/1675; A61B 2090/065
See application file for complete search history.

(56) References Cited

U.S. PATENT DOCUMENTS 10,321,920 B2 *   6/2019   McGinley .......... A61B 17/1633
11,589,940 B2 *   2/2023   Urvoy ................ A61B 17/1626
(Continued)

FOREIGN PATENT DOCUMENTS

EP          512867 A2 *   11/1992    ......... G05B 19/4163
WO     2014/198784 A1     12/2014

*Primary Examiner* — Kevin T Truong
*Assistant Examiner* — Diana Jones
(74) *Attorney, Agent, or Firm* — Condo Roccia Koptiw LLP

(57) ABSTRACT

The disclosure relates to a robotic system for removing bony material from an anatomical structure of a patient, comprising:—a base (4),—an end effector (2) configured to hold a surgical tool (1),—an actuation unit (3) configured to translate the end effector relative to the base at least along one feed axis (A),—a control unit coupled to the actuation unit (3) and configured to turn off the tool (1) and command the actuation unit (3) to translate the end effector (2) along the feed axis (A) while the tool is turned off, the control unit comprising a feedback unit configured to measure a force exerted by the surgical tool (1) onto the anatomical structure during said translation of the end effector (2) and, based on the measured force, detect a contact of the tool with bony material of the anatomical structure.

19 Claims, 4 Drawing Sheets

(51) Int. Cl.
 *A61B 34/00* (2016.01)
 *A61B 90/00* (2016.01)
(52) U.S. Cl.
 CPC .............. *A61B 34/25* (2016.02); *A61B 90/06* (2016.02); *A61B 2090/065* (2016.02)

(56) References Cited

U.S. PATENT DOCUMENTS

| | | | | |
|---|---|---|---|---|
| 2009/0245956 | A1* | 10/2009 | Apkarian | A61B 17/1695 |
| | | | | 408/11 |
| 2016/0151120 | A1* | 6/2016 | Kostrzewski | A61B 90/50 |
| | | | | 606/130 |
| 2017/0128081 | A1* | 5/2017 | McGinley | A61B 17/1695 |

* cited by examiner

ROBOTIC SYSTEM FOR REMOVING BONY MATERIAL FROM AN ANATOMICAL STRUCTURE

CROSS-REFERENCE TO RELATED APPLICATIONS

This application is a national stage application of International Application No. PCT/EP2019/063838, filed on May 28, 2019. International Application No. PCT/EP2019/063838 claims priority to and the benefit of European Application No. 18305649.8, filed May 28, 2018. The entire contents of each of these applications are incorporated herein by reference.

FIELD OF THE INVENTION

The invention relates to a robotic system for removing bony material from an anatomical structure.

BACKGROUND OF THE INVENTION

During knee arthroplasty, the surgeon has to remove bony material from the femur and the tibia to replace it by a prosthesis.

To that end, the surgeon uses a surgical tool, such as a bur.

However, cutting the posterior part of the tibia is a delicate operation since the region of the knee adjacent to the posterior part of the tibia T comprises in particular the femoral artery FA and the articular capsule AC that contains synovial fluid (see FIG. 1), that must not be damaged by the tool. The arrow shows the general cutting direction.

Thus, the surgeon has to make sure that he only removes bone, and to stop the cutting operation before hitting other structures of this region.

However, this can be a challenging task because the posterior part of the bone is not in direct sight of the surgeon during the cut. Indeed, other bony parts, soft tissues, various fluids, or the cutting tool itself will generally hide the posterior situs.

In case of navigated image-based surgery, the surgeon is able to visualize the position of the cutting tool relative to a model of the bone thanks to a 3D image of the region acquired pre-operatively. Such a pre-operative image provides a model of the bone only and not of soft structures that surround the bone and that may deform during the surgical intervention. This model may help the surgeon to stop the cutting tool at the right depth, but it assumes the bone model and its registration with the real anatomy is accurate.

In case of navigated image-free surgery only the bony parts that can be digitized by the surgeon prior to the cut (typically with a localized pointer tool) can be visualized.

At the beginning of the surgical intervention the posterior part of the bone is not easily accessible: digitization is thus often difficult and modelling of the region potentially inaccurate. Later, it may not be suitable to require the surgeon to repeatedly palpate this region to detect whether all the bony material has been removed. Frequent palpation could significantly increase the duration of the surgical intervention.

Another problem may arise from the fact that the tool may not be held in the surgeon's hand but may be held by an active robotic system, meaning that the surgeon does not directly controls operation of the tool.

SUMMARY

The present disclosure attempts to remedy the above-described problems by finding a solution to detect easily whether there remains bony material in an anatomical structure that is being cut by a surgical tool, even if the anatomical structure is not accessible for visual inspection or palpation.

To that end, an object of the systems and methods disclosed herein is to design a robotic system for removing bony material from an anatomical structure of a patient, comprising:
- a base,
- an end effector configured to hold a surgical tool,
- an actuation unit configured to translate the end effector relative to the base at least along one feed axis,
- a control unit coupled to the actuation unit and configured to turn off the tool and command the actuation unit to translate the end effector along the feed axis while the tool is turned off,
- the control unit comprising a feedback unit configured to measure a force exerted by the surgical tool onto the anatomical structure during said translation of the end effector and, based on the measured force, detect a contact of the tool with bony material of the anatomical structure.

According to an embodiment, the robotic system further comprises a user interface configured to display an information relative to the presence of bony material in the anatomical structure along the feed axis.

According to an embodiment, the control unit is configured to prevent turning on the surgical tool if the feedback unit does not detect any contact of the tool with bony material.

The control unit may further be configured to generate an alert if the feedback unit does not detect any contact of the tool with bony material.

According to an embodiment, the control unit is configured to turn off the tool and command the actuation unit to move the end effector along the feed axis at predetermined time or distance intervals.

According to an embodiment, the feedback unit comprises at least one sensor configured to measure intensity of electric current powering the actuation unit, the feedback unit being configured to monitor variation of said intensity over time during the translation of the end effector and detect a contact of the tool with bony material of the anatomical structure if said intensity exceeds a predetermined threshold.

The robotic system may further comprise a support unit connected to the base, comprising at least one element designed to make contact with the anatomical structure or a region of the patient's body adjacent to the anatomical structure so as to provide a partial mechanical link between the tool and the anatomical structure.

The robotic system may further comprise a holding arm having one end rigidly attached to the base and an opposite end configured to be attached to a structure fixed relative to the patient.

According to an embodiment, the robotic system further comprises a tracker rigidly attached to the end effector and adapted to be localized by a localization system, and the feedback unit is configured to take into account localization data of the tracker to detect a contact between the tool and bony material of the anatomical structure.

The robotic system may further comprise a surgical tool configured to remove bony material from the anatomical structure rigidly attached to the end effector.

Advantageously, the surgical tool is a burr, preferably a round burr.

According to an embodiment, wherein the control unit is configured to record at least one physical parameter of the robotic system linked to bone mineral density.

The robotic system may be operated according to the following procedure:
- a tool is mounted onto the end effector;
- the tool is turned on and moved by the actuation unit to partially cut the anatomical structure;
- the tool is then turned off and the end effector is translated along the feed axis;
- a force exerted by the surgical tool onto the anatomical structure during said translation of the end effector is measured by a feedback unit;
- based on the measured force, a contact of the tool with bony material of the anatomical structure may be detected.

Then, if bony material is detected, the tool may be turned on again and moved by the actuation unit to continue cutting the anatomical structure.

On the contrary, if no bony material is detected, turning on the tool may be prevented by the control unit.

BRIEF DESCRIPTION OF THE FIGURES

Further features and advantages of the systems and methods disclosed herein will appear in the following detailed description, with reference to the appended drawings, wherein.

DETAILED DESCRIPTION OF EXEMPLARY EMBODIMENTS

Figure 1:
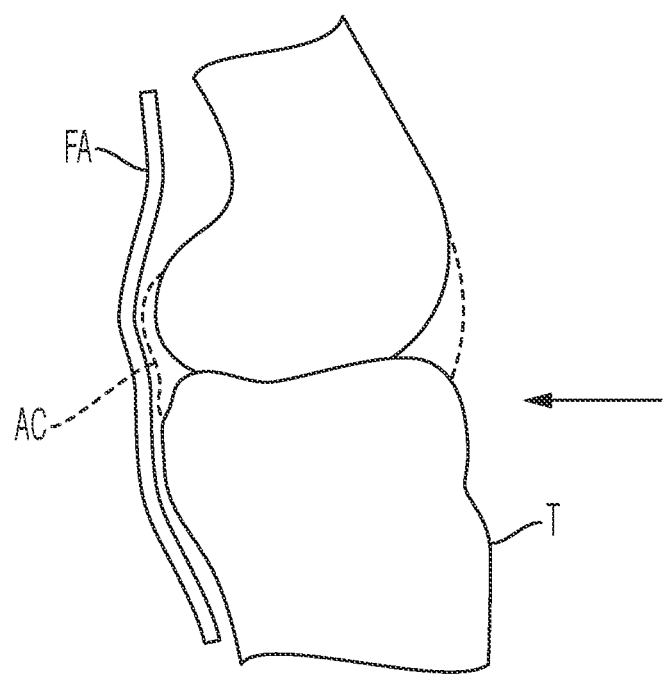
FIG. 1 shows a schematic side cross sectional view of a knee joint.

Although the description that follows is directed to the milling of the posterior part of the tibia using a surgical burr, the description may also apply to other surgical interventions such as spine surgery (e.g. decompression, laminectomy, etc.). The cutting process preferably consists in (but is not limited to) milling a bone; the cutting process may include drilling or sawing the bone.

A robotic system may be configured to carry out the cutting process. The same reference signs are used to designate the same elements throughout FIGS. 2 to 5.

The robotic system comprises an end-effector 2 which is configured to hold a surgical tool 1, such as a burr, a drill or a saw. The surgical tool may be an off-the-shelf tool and will thus not be described in more detail.

According to a preferred embodiment, the surgical tool is a burr.

The robotic system comprises a base 4, which may be held by a user. As explained in further detail below, the base may not be handled solely by hand, but may also be held by an articulated holding arm and/or connected to the tibia by a support unit.

The robotic system further comprises an actuation unit 3 configured to move the end effector 2 relative to the base 4. To that end, the actuation unit may comprise one or several motors capable of moving the end effector according to at least one degree of freedom. At least one degree of freedom consists of a translation of the end effector along a feed axis.

During the cutting operation, the burr is caused to rotate along its own longitudinal axis.

The robotic system further comprises a control unit which is coupled to the actuation unit. The control unit is configured to turn on and turn off the tool (i.e. causing or not rotation of the burr). Besides, the control unit is configured to command the actuation unit to move the end effector.

According to the disclosure, the robotic system is configured to detect presence of bony material in front of the burr, in particular in the posterior region of the tibia.

To that end, the control unit includes a feedback unit that implements a test procedure involving a translation of the tool which is in a turned off state, and evaluation of the mechanical resistance of any material encountered by the end of the tool during this translation.

Such translation may involve only one motor of the actuation unit if the feed axis is substantially parallel to the surface of the bone that has already been cut, which is typically a plane. However, if this is not the case, several motors of the actuation unit may be combined to orient the tool substantially parallel to the cutting plane.

The detection is implemented by measuring a force exerted by the tool during the translation of the end effector (the tool being turned off), and by determining, based on the measured force, whether the tool is in contact with bony material.

The force is in particular linked to the intensity of electrical current necessary to feed the motor to translate the tool along the feed axis toward the bone. Indeed, if the tool is in contact with anatomical tissues, the intensity of electrical current required to push the tool further along the feed axis will increase.

To that end, the robotic system comprises at least one sensor configured to measure this intensity, and the feedback unit is configured to monitor the variation of the current measured by the sensor and to compare the measured intensity with a predetermined threshold.

Said threshold may be fixed arbitrarily, e.g. based on average values that may have been measured prior to the configuration of the robotic system.

Alternatively, the threshold may be determined in situ and thus be specific to the patient to be treated. In this way, the feedback would take into account more precisely variations in bone density from one patient to another one, in particular in case of osteoporosis. To that end, the intensity of electrical current measured during the cutting process that precedes the test procedure may be used to deduce a threshold value adapted to the patient. Otherwise, the surgeon may be required to calibrate the system before beginning the surgical intervention by implementing the test procedure on one or several bony regions of the patient.

Optionally, the robotic system may comprise a user interface (not shown) configured to display information about the measured force and/or the presence of bony material. The user interface may for example comprise a screen coupled to the control unit.

Optionally, the control unit may be configured to generate an alert (e.g. visual or audible) to warn the user in case no bony material is detected.

The control unit may be programmed to launch the test procedure at determined time intervals or distance intervals (e.g. every cm) during the cutting step. Otherwise, the control unit may be configured to launch the test procedure at the end of the cutting step. Alternatively, the test procedure may be launched by the user himself, e.g. thanks to a dedicated switch on the robotic system.

Figure 2:
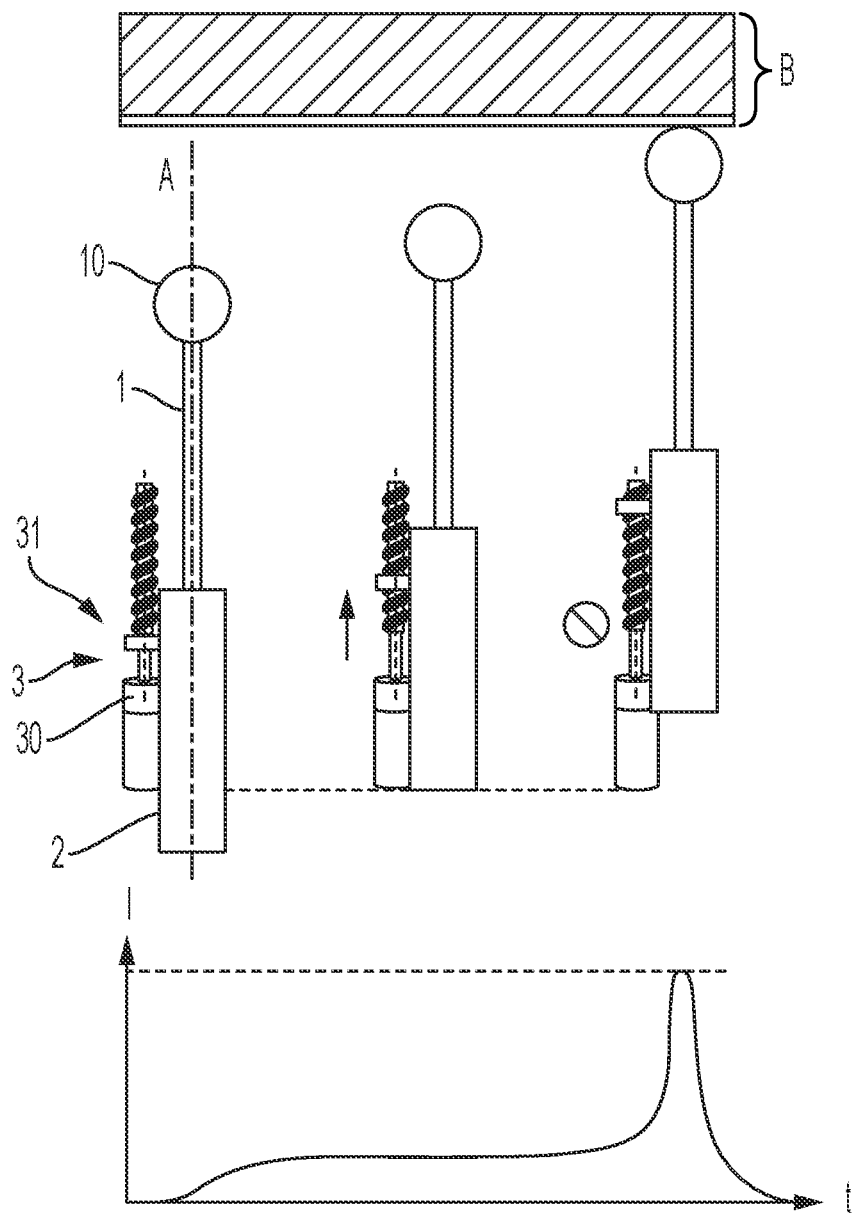
FIG. 2 schematically illustrates an embodiment of the principle of detection of the presence of remaining bone.

FIG. 2 schematically illustrates an embodiment of the principle of detection of the presence of remaining bone on the posterior part of the tibia.

The head 10 of the burr 1 advantageously presents a spherical shape, or any other rounded shape. Preferably, the head does not have a pointed shape in order to avoid any penetration of the head into the bone when a pressure is exerted by the bur onto the bone
instead of increasing this pressure. In case the tool comprises a tip or a tooth that is likely to penetrate into the bone (e.g. a drill or a saw), the feed axis advantageously does not coincide with the direction of said tip or tooth.

The burr 1 is mounted on an end effector 2.

The actuation unit 3 is represented in a simplified way, with a motor 30 coupled to the end effector 2 by a mechanical connection 31 causing the end effector to translate along feed axis A when the motor rotates. It is to be noted that the actuation unit may be more complex and in particular include more than one motor, with different types of mechanical connections with the end effector. A sensor is arranged to measure the current provided to each relevant motor. In the following description, it is assumed that one motor is sufficient to translate the tool and that only the electrical current provided to this motor is measured. However, in case several motors are involved, it is possible to measure the current provided to each motor and to combine the measurements to determine the force exerted by the tool end.

The curve at the bottom of FIG. 2 shows the intensity I of the electrical current feeding the motor of the actuation unit as a function of time t.

During the surgical intervention, the burr 10 is rotated and moved by the actuation unit 3 to cut the tibia according to a cutting plane (not illustrated in FIG. 2).

When it is desired to check whether there remains bony material in the posterior part of the tibia, the control unit turns off the bur and stops the actuation unit. Alternatively, the user himself may turn off the bur and launch the test procedure.

At the beginning of the test procedure, the actuation unit 3 is stopped, no electrical current being provided to the motor 30 (left view of FIG. 2). The intensity I measured by the sensor is thus null.

Once the test procedure has started, the motor 30 is fed with an electrical current whose intensity is substantially constant as long as the burr head 10 does not contact any anatomical structure (middle view of FIG. 2).

When the burr head 10 contacts the surface of the anatomical structure B, the intensity of the electrical current provided to the motor significantly increases (right view of FIG. 2). In case of soft tissues, the intensity will increase more slowly than in case of bony material. If the intensity reaches a predetermined threshold, the control unit determines the presence of bony material, and the operation of the actuation unit is stopped.

Then, the control unit may allow the robotic system to turn the burr on again, to continue the cutting operation.

If the intensity does not reach the predetermined threshold after the burr has traveled for a specified distance, the control unit determines the absence of bony material in the posterior region of the tibia. As a result, the control unit may impede further operation of the cutting tool in this region, in order to reduce the chance of damaging the femoral artery and/or the articular capsule.

Figure 3A:
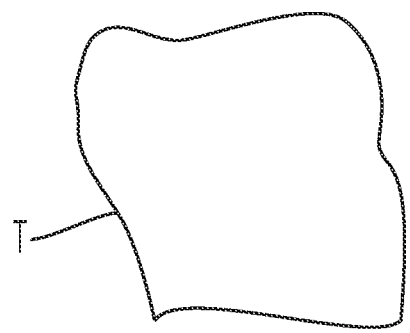
FIGS. 3A to 3C illustrate different steps of use of the robotic system.
Figure 3B:
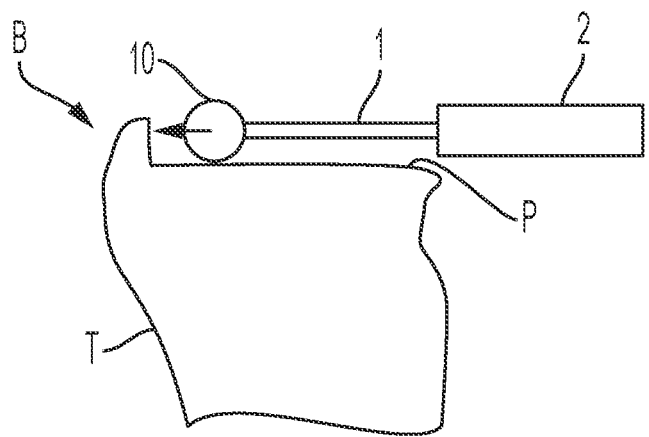
Figure 3C:
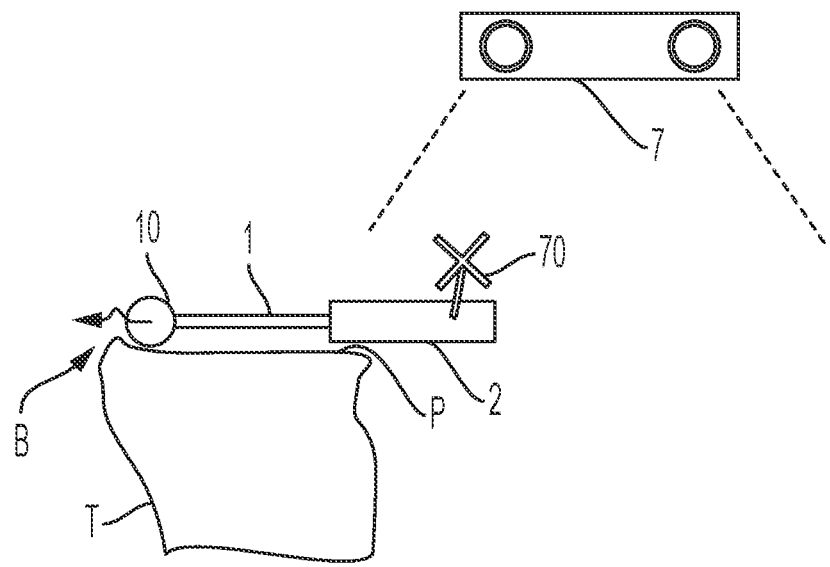

FIGS. 3A to 3C illustrate different steps of use of the robotic system.

FIG. 3A is a side cross sectional view of a tibia T to be cut. The anterior part of the tibia is on the right of the figure; the posterior part of the tibia is on the left of the figure.

FIG. 3B schematically shows the tibia of FIG. 3A after a significant part of the tibia plateau has been removed, defining a cutting plane P. However, there remains a certain amount of bone B in the posterior region of the tibia. In order to detect this remaining amount, the above-described test procedure is implemented. To that end, the burr 1 with a spherical head 10 is translated along the direction indicated by the arrow, substantially parallel to the cutting plane P, until a contact of the head with the surface of the bone B is detected.

FIG. 3C illustrates another situation that may occur after cutting a significant part of the tibial plateau. In some cases, the shape of the amount of bone B remaining in the posterior region of the tibia is such that it does not ensure that the burr head will come into abutment with the surface. For example, in the case illustrated in FIG. 3C, the height of the bone material extending above the cutting plane P is too small to block the burr head. As a result, the burr head may slide along the surface and thus pass over the remaining bone material (trajectory represented by the distorted arrow). In such case, the test procedure might not provide an accurate result.

In order to improve the accuracy of the detection, a navigation system may be used. To that end, a tracker 70 is rigidly attached to the end effector 2. Said tracker is localized by a localization system 7, which thus allows determining the position of the burr head.

By comparing the position of the burr head as determined by the localization system and the position of the expected remaining bone material, it is possible to determine whether the burr head has reached the remaining bone following the predetermined path, and to deduce therefrom the presence or absence of bony material, or the validity of the test procedure and its result.

The localization data may be used alone (i.e. without any measurement of the intensity of the electrical current provided to the motor) or in combination with said measurement, to provide redundant information.

The embodiments disclosed herein may provide more accurate results when there is a mechanical link between the bone and the end effector. This mechanical link may be provided by a support unit connecting the base of the robotic device to the tibia (see FIG. 4) and/or by an articulated holding arm that rigidly connects the base of the robotic device to a fixed element of the operating room (see FIG. 5).

Figure 4:
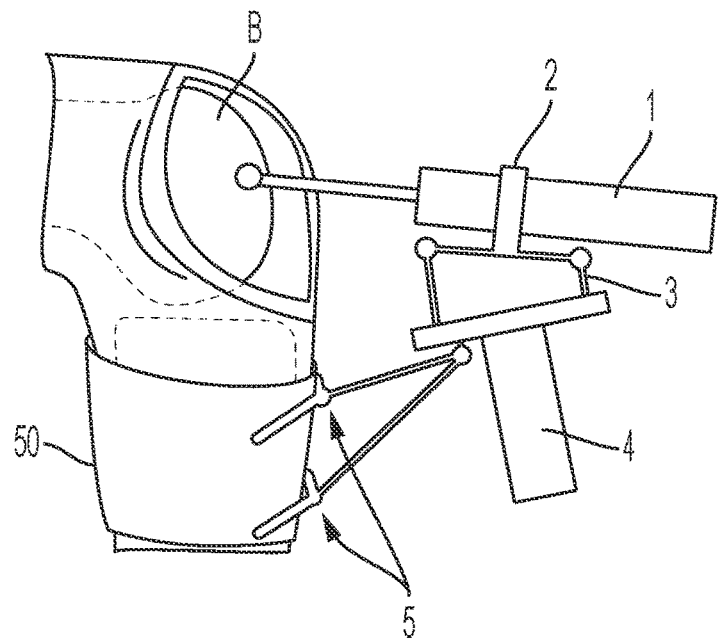
FIG. 4 illustrates an embodiment of the robotic system including a support unit creating a partial mechanical link with the bone to be cut.

With reference to FIG. 4, a strap 50 is placed around a part of the leg to compress the soft tissues surrounding the bone. Two V-shaped pins 5 extend from the base 4 of the robotic system and the strap 50, thus creating a partial mechanical link between the tool and the bone. Of course, other support units, described in particular in documents WO 2014/198784 and WO 2014/198796 could be used.

Figure 5:
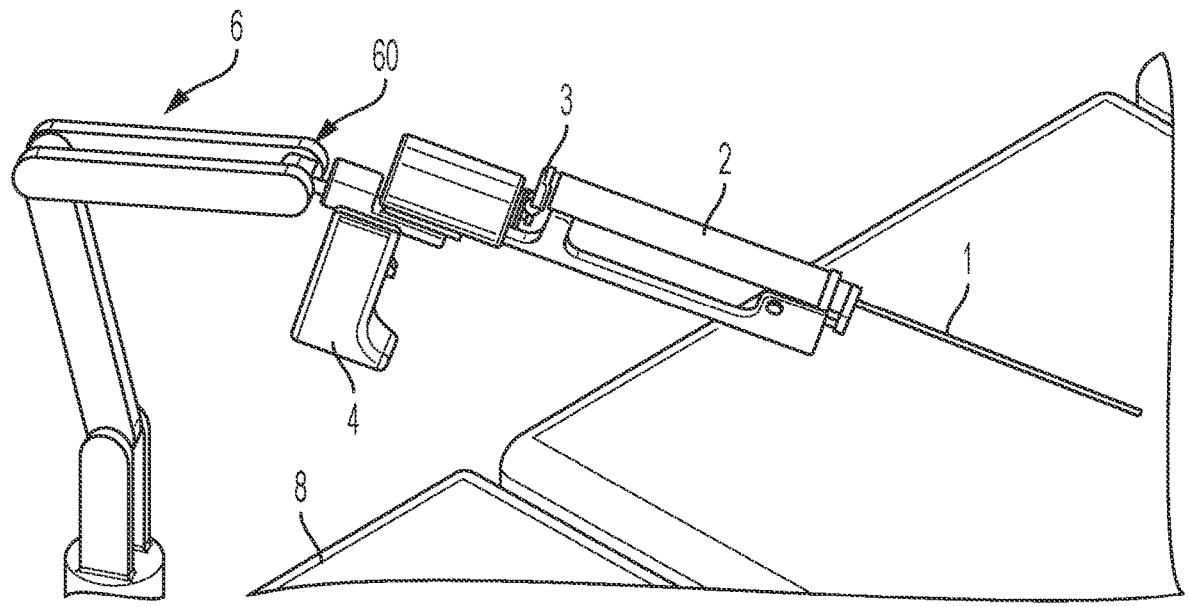
FIG. 5 illustrates an embodiment of the robotic system whose base is held by a holding arm.

With reference to FIG. 5, the robotic system may be held by a holding arm 6. The arm comprises one end rigidly attached to a fixed structure such as the operating table 8, and an opposite end 60 rigidly connected to the base 4. The holding arm is articulated with several degrees of freedom and includes a switch that allows braking or freezing its position once the base 4 is in a position suitable for the surgical intervention. Various technologies may be employed (pneumatic arms, hydraulic arms, mechanical arms, arms with brakes, etc.).

The detection procedure described above could also be advantageously used with another goal. During the surgical intervention, at least one first tracker is fixed to the patient (e.g. to the bone to be cut or to an adjacent bone) and at least one second tracker is fixed to the robotic system, e.g. to the end effector, in order to localize the end effector relative to the patient. The first tracker is supposed to be rigidly fixed to the patient during the whole surgical intervention; however, in some cases, in particular when a shock is applied to the tracker, the tracker may move relative to the patient, resulting in a wrong positioning of the end effector relative to the bone to be cut. In order to detect such a situation, the user may be required to place the robotic system in an initial position before starting the cutting process, and the control unit may launch a bone detection procedure by commanding the actuation unit to bring the surgical tool to several regions that are supposed to comprise bony material (based on a numerical model of the bone). If the feedback unit detects the presence of bony material at each expected position, one may consider that the numerical model of the bone is correct and that the relative position of the robotic system and the bone is correct. On the contrary, if the feedback unit detects bony material in a region where such bony material was not expected, or if the feedback unit does not detect bony material in a region where bony material should be present, one may conclude that the numerical model of the bone is inaccurate or that the position of the robotic system relative to the bone is erroneous. In such case, the control unit may generate an alert and/or impede any actuation of the surgical tool.

According to an embodiment, the control unit may record at least one physical parameter of the robotic system linked to bone mineral density (BMD). Such a parameter can be electrical currents used for displacement of the cutting tool as described above, or a level of the electrical current used to actuate the cutting tool itself (e.g. current required for the burr rotation). This recording can be done either continuously during the normal bone cutting process, or after the cut, by pressing the cut surface with the tool on different points. Thus, the control unit may create and display a map of the value of the electrical current recorded, or the result of the computation based on several current levels, enabling visualization of the record at various locations of the cut surface. This map may then be interpreted as a "bone density map", which may be used as an input for another application. An algorithm may be required to interpret and correct the data, e.g. considering that the displacement load may be different in one direction and the opposite direction while the burr is rotating always in the same direction or considering that the cutting tool may also wear off during the procedure, which can affect the current levels.

The invention claimed is:

1. A robotic system, comprising:
an end effector retaining a rotatable burr, wherein when the burr is turned on, the burr removes bony material from an anatomical structure of a patient; and
a control unit configured to:
turn off the burr;
while the burr is off, translate the burr along a feed axis;
determine an intensity of electrical current necessary to translate the burr tool along the feed axis while the burr is off; and
monitor the intensity, wherein:
if the intensity reaches a predetermined threshold, the control unit determines the burr has contacted bony material.

2. The robotic system of claim 1, wherein the control unit is further configured to, if the intensity reaches the predetermined threshold, stop translating the burr along the feed axis.

3. The robotic system of claim 2, wherein the control unit is further configured to allow the burr to be turned on again.

4. The robotic system of claim 1, wherein the control unit is further configured to prevent the burr from being turned on again unless the control unit has determined that the burr has contacted bony material.

5. The robotic system of claim 1, wherein, if the intensity increases at a rate below a predetermined rate associated with bone, the control unit is further configured to determine the burr has contacted soft tissue and to prevent the burr from being turned on again.

6. The robotic system of claim 5, wherein the control unit is further configured to generate an alert if the intensity does not reach the predetermined rate.

7. The robotic system of claim 1, wherein, if the intensity does not reach the predetermined threshold after the burr has traveled a predetermined distance, the control unit is further configured to determine that no bony material is present and to prevent the burr from being turned on again.

8. The robotic system of claim 7, wherein the control unit is further configured to generate an alert if the intensity does not reach the predetermined threshold.

9. The robotic system of claim 1, wherein the control unit is further configured to generate an alert if the intensity does not reach the predetermined threshold.

10. The robotic system of claim 1, wherein the control unit is further configured to record at least one physical parameter of the robotic system linked to bone mineral density.

11. The robotic system of claim 1, further comprising a user interface configured to display information based on whether the control unit has determined at least one of that the burr has contacted bony material or that no bony material is present.

12. The robotic system of claim 1, wherein the control unit is further configured to turn off the burr and translate the burr along the feed axis at predetermined time intervals.

13. The robotic system of claim 1, wherein the control unit is further configured to turn off the burr and translate the burr along the feed axis at predetermined distance intervals.

14. The robotic system of claim 1, further comprising an actuation unit operably connected to the control unit, wherein the actuation unit is configured to translate the end effector, and therefore the burr, along the feed axis.

15. The robotic system of claim 14, wherein the intensity of electrical current necessary to translate the burr is determined as an intensity of electric current powering the actuation unit as the actuation unit translates the end effector, and therefore the burr, along the feed axis.

16. The robotic system of claim 14, further comprising a base attached to the actuation unit.

17. The robotic system of claim 16, further comprising a support unit to make contact with the patient's body to provide a partial mechanical link between the patient and the base.

18. The robotic system of claim 16, further comprising a holding arm having one end configured to be attached to a structure fixed relative to the patient and an opposite end connected to the base.

19. The robotic system of claim 1, further comprising a tracker attached to the end effector and a localization system for detecting the tracker.

* * * * *